(12) United States Patent
Waugh et al.

(10) Patent No.: US 12,337,065 B2
(45) Date of Patent: *Jun. 24, 2025

(54) COMPOSITIONS FOR TREATING VIRAL INFECTIONS AND METHODS FOR SAME

(71) Applicant: Access to Advanced Health Institute, Seattle, WA (US)

(72) Inventors: Jacob Waugh, Irvine, CA (US); Jonah Shacknai, Santa Barbara, CA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/817,963

(22) Filed: Aug. 5, 2022

(65) Prior Publication Data

US 2022/0370360 A1 Nov. 24, 2022

Related U.S. Application Data

(63) Continuation of application No. 17/472,750, filed on Sep. 13, 2021, now Pat. No. 11,433,028, which is a continuation of application No. 17/304,343, filed on Jun. 18, 2021, now abandoned.

(60) Provisional application No. 63/065,754, filed on Aug. 14, 2020.

(51) Int. Cl.
*A61K 9/16* (2006.01)
*A61K 31/485* (2006.01)
*C07K 1/00* (2006.01)

(52) U.S. Cl.
CPC .......... *A61K 9/1647* (2013.01); *A61K 31/485* (2013.01); *C07K 1/00* (2013.01)

(58) Field of Classification Search
CPC .................................................. A61K 9/1647
See application file for complete search history.

(56) References Cited

U.S. PATENT DOCUMENTS

| | | | |
|---|---|---|---|
| 8,022,179 | B2 | 2/2011 | Dake et al. |
| 10,729,735 | B1 | 8/2020 | Newman et al. |
| 10,744,189 | B2 | 8/2020 | Schluch et al. |
| 11,433,028 | B2 | 9/2022 | Waugh et al. |
| 2005/0153841 | A1 | 7/2005 | Bunt et al. |
| 2006/0018867 | A1 | 1/2006 | Kawasaki et al. |
| 2009/0029924 | A1 | 1/2009 | Strongin et al. |
| 2020/0197288 | A1* | 6/2020 | Gudmundsdottir ..... A61P 29/00 |
| 2021/0401751 | A1 | 12/2021 | Waugh et al. |
| 2023/0081039 | A1 | 3/2023 | Zhang et al. |

FOREIGN PATENT DOCUMENTS

| | | | |
|---|---|---|---|
| IN | 307/KOL/2010 | 2/2016 | |
| WO | WO-2007046781 A1 * | 4/2007 | ............... C07K 7/06 |
| WO | 2022029577 | 2/2022 | |
| WO | WO 2022/029577 A1 | 2/2022 | |

OTHER PUBLICATIONS

Hosoya et al (Antiviral Chemistry & Chemotherapy vol. 2 (4), pp. 243-248) (Year: 1991).*
Cheng et al., "Furin Inhibitors Block SARS-CoV-2 Spike Protein Cleavage to Suppress Virus Production and Cytopathic Effects", Cell Reports, vol. 33, No. 2, Art. 108254, 18 pages (2020).
Coutard et al., "The spike glycoprotein of the new coronavirus 2019-nCoV contains a furin-like cleavage site absent in CoV of the same clade", Antiviral Res., vol. 176, No. 104742, 6 pages (2020).
Couture et al., "On the cutting edge of proprotein convertase pharmacology: from molecular concepts to clinical applications", Biomol. Concepts, vol. 2, No. 5, pp. 421-438 (2011)
Cramer et al., "Poly-L-lysine Glycoconjugates Inhibit DC-SIGN-mediated Attachment of Pandemic Viruses", ChemRxiv, Preprint, Article downloaded from https://doi.org/10.26434/chemrxiv.13072025.v1, 32 pages (2020).
Dahlen et al., "Inhibition of soluble recombinant furin by human proteinase inhibitor 8", J. Biol. Chem., vol. 273, No. 4, pp. 1851-1854 (1998).
Farag et al., "Identification of FDA Approved Drugs Targeting COVID-19 Virus by Structure-Based Drug Repositioning", ChemRxiv, pp. 1-20 (2020).
Huijghebaert et al. "Does Trypsin Oral Spray (Viruprotect®/ColdZyme®) Protect against COVID-19 and Common Colds or Induce Mutation? Caveats in Medical Device Regulations in the European Union", Int. J. Environ. Res. Public Health, vol. 18, No. 10, Art. 5066, 15 pages (2021).
International Search Report from International Application No. PCT/US2022/018379, 7 pages, Mailed Nov. 2, 2022.
Langeland et al., "Interaction of polylysine with the cellular receptor for herpes simplex virus type 1", J. Gen. Virol., vol. 69, Pt. 6, pp. 1137-1145 (1988).
Palit et al., "Phytopharmaceuticals mediated Furin and TMPRSS2 receptor blocking: can it be a potential therapeutic option for Covid-19?", Phytomedicine, vol. 85, No. 153396, 21 pages (2021).
Paull et al., "Virucidal and antiviral activity of astodrimer sodium against SARS-CoV-2 in vitro", Antiviral Res., vol. 191, No. 105089, 8 pages (2021).
Seigfried et al., "Regulation of the stepwise proteolytic cleavage and secretion of PDGF-B by the proprotein convertases", Oncogene, vol. 24, No. 46, pp. 6925-6935 (2005).
Stagi et al., "Effective SARS-CoV-2 antiviral activity of hyperbranched polylysine nanopolymers", Nanoscale, Royal Society of Chemistry, vol. 13, No. 39, pp. 16465-16476 (2021).
Chen, et al., "Furin Inhibitors Black SARA-C0V-2 Spike Protein Cleavage to Suppress Virus Production and Cytopathic Effects," Cell Reports 33, 108254, Oct. 13, 2020, 18 pages.
Couture, et al., "On the cutting edge of proprotein convertase pharmacology: from molecular concepts to clinical applications," Bimol Concepts. Oct. 1, 2011;2(5): 421-438.
Siegfried, et al., "Regulation of the stepwise proteolytic cleavage and secretion of PDGF-B by the proprotein convertases," Onogene (2005), 24, 6925-6953, 11 pages.
Dahlen, et al., "Inhibition of Soluble Recombinant Furin by Human Proteinase Inhibitor 8*," The Journal of Biological Chemistry, vol. 273, No. 4, Issue of Jan. 23, 1998, pp. 1851-1854.

(Continued)

*Primary Examiner* — Albert M Navarro
(74) *Attorney, Agent, or Firm* — Benjamin Keim; Newport IP, LLC (57) ABSTRACT

Compositions containing a protease inhibitor for treating viral infections and methods for treating a patient before, during, or after exposure to an infectious agent by administering such compositions are described herein.

20 Claims, 5 Drawing Sheets

Specification includes a Sequence Listing.

(56) References Cited

OTHER PUBLICATIONS

Palit, et al., "Phytopharmaceuticals mediated Furin and TMPRSS2 receptor blocking; can it be a potential therapeutic option for Covid-19?", Phytomedicine 85 (2021) 153396, 21 pages.

Huijghebaert, et al., "Does Trypsin Oral Spray (Vituprotect(R)/ColdZyme(R)) Protect against COVID-19 and Common Colds or Induce Mutation? Caveats in Medical Device Regulations in the European Union," Int. J. Environ. Red. Public Health 2021, 18, 5066. https://doi.org/10.3390/ijerph1815066.

Paull, et al., "Virucidal and antivaral activity of astrodrimer sodium against SARS-CoV-2 in vitro," May 16, 2021, published by Eselvier B., V., 8 pages.

Langeland, "Interaction of Polylysine with the Cellular Receptor for Herpes Simplex Virus Type 1," JJ. ge. Virol. (1988), 69, 1137-1145, 10 pages.

Coutard, et al., "The spike glycoprotein of the new coronavirus 2019-nCoV contains a furin-like cleavage site absent in CoV of the same clade," retrieved from the Internet: URL:https://www.ncbi.nlm.nih.gov/labs/pmc/articles/PMC7114094/pdf/main.pdf [retrieved on Aug. 16, 2021], 33 pages.

International Search Report and Written Opinon for related application PCT/US2022/018379 mailed Nov. 2, 2023, 33 pages.

Vienot, et al., "Effective SARS-CoV-2 antiviral activity of hyperbranched polylysine nanopolymers," Nanoscale, vol. 13, Oct. 21, 2021, pp. 16465-16476, XP055940974.

\* cited by examiner

COMPOSITIONS FOR TREATING VIRAL INFECTIONS AND METHODS FOR SAME

CROSS-REFERENCE TO RELATED APPLICATIONS

This application is a continuation of U.S. patent application Ser. No. 17/472,750, filed Sep. 13, 2021, now allowed, which is a continuation of U.S. application Ser. No. 17/304,343, filed Jun. 18, 2021, which claims the benefit of U.S. Provisional No. 63/065,754, filed Aug. 14, 2020, each of which is hereby incorporated by reference in its entirety.

BACKGROUND

Furin is a cellular endoprotease and a member of the proprotein convertase family that is ubiquitously expressed in human tissues. Expression levels of furin vary amongst different tissues and can be quite low depending on tissue types. Furin proteases are abundant in the respiratory tract, and under certain conditions, such as viral infections, furin expression is elevated.

The spike glycoprotein of severe acute respiratory viruses ("SARS viruses") including COV-2 and COVID-19 contains a potential cleavage site for furin proteases that is necessary for entry of the virus into the cell. The membrane of coronaviruses contains a trimeric transmembrane spike glycoprotein (S protein) that contains two functional domains: a receptor binding domain, and a fusion domain that mediates fusion of the viral membrane to the host cell membranes. The S protein must be cleaved by cell proteases to enable exposure of the fusion domain to the host cell membrane. Thus, host protease mediated cleavage of the fusion domain is necessary for SARS viruses to infect host cells. In the case of SARS viruses, furin proteases may perform the necessary cleavage of the fusion domain.

Polylysine has been demonstrated to possess a wide spectrum antimicrobial activity with lesser toxicity to the human system. Poly-L-lysine polymers can be used in promoting cell adhesion to solid substrates, conjugation to methotrexate for increased drug transport, microencapsulation of islets, cell microencapsulation technology, microarray glass slide coating, and chromosomal preparations.

SUMMARY OF THE INVENTION

Various embodiments are directed to methods for treating SARS infections including COVID-19 infection, by administering to a subject in need of treatment a composition containing a protease inhibitor or a furin binding compound and a pharmaceutically acceptable carrier. In some embodiments, administering can be carried out by topical administration to an eye, ear, or nose of the subject, and in certain embodiments, administering can be carried out by intranasal spray. In some embodiments, the methods may include repeating administering at least once per day. The methods of various embodiments may reduce viral load in patient sputum, lung tissue, or blood plasma by at least about 20%, and may improve time to recovery time and survival rate by at least about 20%. The methods of various embodiments may further reduce the long term effects of SARS infection.

In some embodiments, the protease inhibitor or furin binding compound may be a competitive inhibitor of one or more endoproteases, and in some embodiments, the protease inhibitor or furin binding compound may be a polycation. In particular embodiments, the protease inhibitor or furin binding compound is selected from the group consisting of peptide, peptide analog, or peptidomimetic, and in certain cases, the peptide, peptide analog, or peptidomimetic may be an amino acid sequence selected from the group consisting of RGRR (SEQ ID NO:1), RKRKKR (SEQ ID NO:2), RKKR (SEQ ID NO:3), RRRKKR (SEQ ID NO:4), and combinations thereof. In some embodiments, the peptide, peptide analog, or peptidomimetic may be polylysine, α-polylysine, or ε-polylysine. In some embodiments, the protease inhibitor or furin binding compound may be candoxatril, candoxatrilat, dexecadotril (retorphan), ecadotril (sinorphan), racecadotril (acetorphan), sacubitril, sacubitril, thiorphan, UK-414,495, aladotril, alatriopril, daglutril, fasidotril, gemopatrilat, ilepatril, ketalorphan, omapatrilat, phosphoramidon, RB-101, sampatrilat, spinorphan, dynorphin, trypsin, aloxistatin, camostat, ecallantide, leupeptin, nafamostat, pacifastins, patamostat, pepstatin, sepimostat, sivelestat, talopeptin, ulinastatin, upamostat, aliskiren, cipro keren, detikinet, enalkiren, pepstatin, remikiren, terlakiren, zankiren, or combinations thereof. In various embodiments, the protease inhibitor or furin binding compound may be about 95% (w/w) to about 5% (w/w) furin binding compound based on the total weight of the composition. the composition further comprises an antiviral agent or anti-inflammatory agent.

In some embodiments, the methods may further include administering an antiviral agent or an anti-inflammatory agent with the composition, and in such embodiments, administering the antiviral agent or anti-inflammatory agent can be carried out simultaneously or sequentially with the compositions of the invention. In certain embodiments, administering the antiviral agent or anti-inflammatory agent can be carried out by oral administration or injection.

Further embodiments are directed to methods for treating SARS infections including COVID-19 infection, by prophylactically administering to a subject in need of treatment a composition containing a protease inhibitor or a furin binding compound and a pharmaceutically acceptable carrier. In some embodiments, administering can be carried out by topical administration to an eye, ear, or nose of the subject, and in certain embodiments, administering can be carried out by intranasal spray. In some embodiments, the methods may include repeating administering at least once per day. The methods of various embodiments may reduce viral load in patient sputum, lung tissue, or blood plasma by at least about 20%, and may improve time to recovery time and survival rate by at least about 20%. The methods of various embodiments may further reduce the long term effects of SARS infection.

In some embodiments, the protease inhibitor or furin binding compound may be a competitive inhibitor of one or more endoproteases, and in some embodiments, the protease inhibitor or furin binding compound may be a polycation. In particular embodiments, the protease inhibitor or furin binding compound is selected from the group consisting of peptide, peptide analog, or peptidomimetic, and in certain cases, the peptide, peptide analog, or peptidomimetic may be an amino acid sequence selected from the group consisting of RGRR (SEQ ID NO:1), RKRKKR (SEQ ID NO:2), RKKR (SEQ ID NO:3), RRRKKR (SEQ ID NO:4), and combinations thereof. In some embodiments, the peptide, peptide analog, or peptidomimetic may be polylysine, α-polylysine, or ε-polylysine. In some embodiments, the protease inhibitor or furin binding compound may be candoxatril, candoxatrilat, dexecadotril (retorphan), ecadotril (sinorphan), racecadotril (acetorphan), sacubitril, sacubitril, thiorphan, UK-414,495, aladotril, alatriopril, daglutril, fasidotril, gemopatrilat, ilepatril, ketalorphan, omapatrilat, phosphoramidon, RB-101, sampatrilat, spinorphan, dynorphin, trypsin, aloxistatin, camostat, ecallantide, leupeptin, nafamostat, pacifastins, patamostat, pepstatin, sepimostat, sivelestat, talopeptin, ulinastatin, upamostat, aliskiren, ciprokeren, detikinet, enalkiren, pepstatin, remikiren, terlakiren, zankiren, or combinations thereof. In various embodiments, the protease inhibitor or furin binding compound may be about 95% (w/w) to about 5% (w/w) furin binding compound based on the total weight of the composition. the composition further comprises an antiviral agent or anti-inflammatory agent.

In some embodiments, the methods may further include administering an antiviral agent or an anti-inflammatory agent with the composition, and in such embodiments, administering the antiviral agent or anti-inflammatory agent can be carried out simultaneously or sequentially with the compositions of the invention. In certain embodiments, administering the antiviral agent or anti-inflammatory agent can be carried out by oral administration or injection.

DESCRIPTION OF THE DRAWINGS

Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention. In the following description, numerous specific details are set forth in order to provide a thorough understanding of the present invention. The present invention may be practiced without some or all of these specific details. In other instances, well known process operations have not been described in details so as to not unnecessarily obscure the present invention.

FIG. 1 is a schematic illustrating the experimental design for the studies described in the Examples.

FIG. 2 is a plot of survival over time of mice administered intranasal polylysine (Treatment) versus mice that were administered saline.

FIG. 3A is a graph showing the daily weight of individual surviving mice following exposure to 60,000 pfu SARS-COV2 and treatment.

FIG. 3B is a graph showing the average daily weight of surviving mice following exposure and treatment.

FIG. 4 is a bar graph showing viral load of mice administered intranasal polylysine (TIGR-001) versus mice administered saline on day 2 after exposure to 10,000 pfu SARS-COV2 and day 4 after exposure to 10,000 pfu SARS-COV2.

FIG. 5 is a graph showing the daily weight of individual surviving mice following exposure to 10,000 pfu SARS-COV2 and treatment.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, 2 μm, 3 μm, 4 μm, 5 μm, 6 μm, and 7 μm are also intended to be explicitly disclosed, as well as the range of values greater than or equal to 1 μm and the range of values less than or equal to 8 μm.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g. "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55," "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government or listed in the U.S. Pharmacopeia or other generally recognized pharmacopeia for use in mammals (e.g. animals), and more particularly, in humans.

"Amino acids" are organic compounds that combine through peptide bond formation to form peptides and proteins. Amino acids can chemically combine through peptide bond formation to form dipeptides, tripeptides, tetrapeptides, oligopeptides, polypeptides, peptides, and proteins. Amino acids are the building blocks for living organisms. The human body uses amino acids to break down food, grow, repair body tissue, and perform other necessary biological processes. The amino acid is not limited, and can be at least one member selected from the group consisting of L-arginine, D-arginine, L-histidine, D-histidine, L-lysine, D-lysine, L-aspartic acid, D-aspartic acid, L-glutamic acid, D-glutamic acid, D-serine, L-serine, D-threonine, L-threonine, D-asparagine, L-asparagine, L-glutamine, D-glutamine, L-cystine, D-cysteine, L-selenocysteine, D-selenocysteine, L-glycine, D-glycine, L-proline, D-proline, L-alanine, D-alanine, L-valine, D-valine, L-isoleucine, D-isoleucine, L-leucine, D-leucine, L-methionine, D-methionine, L-phenylalanine, D-phenylalanine, L-tyrosine, D-tyrosine, L-tryptophan, D-tryptophan.

A "peptidomimetic" is a synthetic chemical compound that has substantially the same structure and/or functional characteristics of a peptide of the invention, the latter being described further herein. Typically, a peptidomimetic has the same or similar structure as a peptide of the invention, for example the same or similar sequence of a casein or fragment thereof. A peptidomimetic generally contains at least one residue that is not naturally synthesized. Non-natural components of peptidomimetic compounds may be according to one or more of: a) residue linkage groups other than the natural amide bond ('peptide bond') linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. Peptidomimetics can be synthesized using a variety of procedures and methodologies described in the scientific and patent literatures, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

The term "salts" as used herein embraces pharmaceutically acceptable salts commonly used to form alkali metal salts of free acids and to form additional salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylate, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, alginic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

As used herein, the term "pharmaceutically acceptable carrier" refers to any of the standard pharmaceutical carriers including, but not limited to non-toxic solvent, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments of the invention are directed to compositions that include endoprotease inhibitors for treating viral infections and methods for using such compositions to treat, prevent, and ameliorate viral infections. Such compositions may further include various excipients that facilitate oral, topical, or both oral and topical administration. The compositions and methods of the invention may reduce outbreaks, symptoms, viral shedding, and proliferation of viral infections by reducing viral loads and targeting sites of viral replication.

The compositions of embodiments described above may be administered to the nose, mouth, eyes, or ears of a subject. In various embodiments, the step of administering can be carried out before, during, or after exposure to an infectious agent, such as a virus or bacteria. In certain embodiments, the compositions of the invention may be used prophylactically to hinder or eliminate host protease mediated cleavage of viral particles necessary to infect host cells. For example, prophylactically administered polylysine protease inhibitor containing compositions have been shown to eliminate COVID-19 infections in individuals repeatedly exposed to the COVID-19 virus for both healthy and high risk subjects. Without wishing to be bound by theory, the protease inhibitor may inhibit endoproteases that cleave viral particles during infection of the host. Endoprotease inhibition can be caused by occupying the active site of the endoprotease passively, by, for example, flooding host cells with endoprotease substrate, actively by irreversibly binding to the active site of the endoproteases, or otherwise inhibiting endoprotease activity by for example, blocking conformational changes necessary for activity. The term "protease inhibitor" as used herein encompasses all of these modes of inhibition and others not specifically identified.

The protease inhibitors of various embodiments may be in any form. In some embodiments, the protease inhibitor may be a peptide, peptide analog, or peptidomimetic. In some embodiments, the protease inhibitor may be a peptide, peptide analog, or peptidomimetic may be nonspecific, meaning the amino acid sequence of the peptide, peptide analog, or peptidomimetic is random and contains no known target sequence. Such nonspecific peptides, peptide analogs, and peptidomimetics may bind to and block activity of endoproteases, including, for example, ACE2 and furin and inhibit the cleavage of viral particles by these endoproteases. In various embodiments, the peptides, peptide analogs, and peptidomimetics may include natural or unnatural amino acids or amino acid analogs which may or may not be synthetic. The number of amino acids included in such peptides, peptide analogs, and peptidomimetics can vary and may be from about 2 to about 100, about 4 to about 75, about 4 to about 50, about 4 to about 25, or any range or individual number of amino acids encompassed by these example ranges.

The peptides, peptide analogs, and peptidomimetics may include a sequence known to bind to endoproteases such as ACE2 and furin. In some embodiments, such sequences may directly inhibit activity of endoproteases by competitively binding to the active site of the endoprotease reducing the ability of the endoprotease to bind to and cleave viral particles. Competitive inhibitor peptides, peptide analogs, and peptidomimetics may include modifications that prohibit cleavage of the sequence target sequence or trap the endoprotease in an intermediate state blocking activity. Such competitive inhibitors may include one or more endoprotease target sequences, which can be target sequences for the same or different endoproteases. Without wishing to be bound by theory, overall endoprotease inhibition of competitive inhibitors having multiple target sequences may be greater than inhibition of competitive inhibitors having a single target sequence, providing equivalent activity to single target sequence competitive inhibitors at a lower dose. In various embodiments, the peptides, peptide analogs, and peptidomimetics may include natural or unnatural amino acids or amino acid analogs which may or may not be synthetic. The number of amino acids included in such peptides, peptide analogs, and peptidomimetics can vary and may be from about 2 to about 100, about 4 to about 75, about 4 to about 50, about 4 to about 25, or any range or individual number of amino acids encompassed by these example ranges.

In other embodiments, the peptides, peptide analogs, and peptidomimetics may include endoprotease target sequences, making them a substrate for the endoprotease such as, for example, ACE2 and furin. In such embodiments, the peptides, peptide analogs, and peptidomimetics may flood exposed tissue with substrate reducing the likelihood that a viral particle may be cleaved and infect cells of the exposed tissue. Such substrate inhibitors may include one or more endoprotease target sequences, which can be substrate for the same or different endoproteases. Without wishing to be bound by theory, overall endoprotease inhibition of substrate inhibitors having multiple target sequences may be greater than inhibition of substrate inhibitors having a single target sequence, providing equivalent activity to single target sequence competitive inhibitors at a lower dose. In various embodiments, the peptides, peptide analogs, and peptidomimetics may include natural or unnatural amino acids or amino acid analogs which may or may not be synthetic. The number of amino acids included in such peptides, peptide analogs, and peptidomimetics can vary and may be from about 2 to about 100, about 4 to about 75, about 4 to about 50, about 4 to about 25, or any range or individual number of amino acids encompassed by these example ranges.

In some embodiments, the peptides, peptide analogs, and peptidomimetics may be modified to include, for example, C-terminal modifications or N-terminal modifications, such as the addition of a protecting group. Suitable protecting groups include, but are not limited to, 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. Side chain protecting groups may also be incorporated into the peptides, peptide analogs, or peptidomimics. Side chain protecting groups include, for example, 2,2,5,7,8-pentamethylchroman-6-sulfonyl (pmc), nitro, p-toluenesulfonyl, 4-methoxybenzene-sulfonyl, Cbz, Boc, adamantyloxycarbonyl, benzyl, o-bromobenzyloxycarbonyl, 2,6-dichlorobenzyl, isopropyl, t-butyl (t-Bu), cyclohexyl, cyclopenyl, acetyl (Ac), and tetrahydropyranyl, trityl, p-toluenesulfonyl, 2,4-dinitrophenyl, formyl, triphenylmethyl(trityl), and the like and combinations thereof. In some embodiments, the peptides, peptide analogs, and peptidomimetics may include linking groups or reactive groups such as alkyl moieties, alkoxy moiety, alkenyl moiety, alkynyl moiety or amino moiety substituted by alkyl moieties, cycloalkyl moiety, polycyclic moiety, aryl moiety, polyaryl moieties, substituted aryl moieties, heterocyclic moieties, substituted heterocyclic moieties, poly ethoxy amino acids, such as AEA ((2-amino) ethoxy acetic acid) or AEEA ([2-(2-amino)ethoxy]ethoxy acetic acid, and the like and combinations thereof. In further embodiments, the peptides, peptide analogs, and peptidomimetics may be conjugated to other proteins or peptides, polymers, such as polyethylene glycol (PEG), lipids, and the like and combinations thereof.

While embodiments of the invention including peptides, peptide analogs, and peptidomimetics are not limited to peptides, peptide analogs, and peptidomimetics of any specific sequence, In some embodiments, the peptides, peptide analogs, and peptidomimetics may include a sequence that is known to bind to furin such as, RGRR (SEQ ID NO:1), RKRKKR (SEQ ID NO:2), RKKR (SEQ ID NO:3), RRRKKR (SEQ ID NO:4), and the like and combinations thereof. In some embodiments, such sequences may be incorporated into larger peptides, which may or may not include furin binding site sequences, and in further embodiments, the sequences may be modified by any of the means discussed above. In certain embodiments, the peptides, peptide analogs, and peptidomimetics may be polylysine. Polylysine is a homopolypeptide belonging to the group of cationic polymers that can be α-polylysine or ε-polylysine. α-Polylysine is a synthetic polymer that can be composed of either L-lysine or D-lysine, resulting in poly-L-lysine (PLL) and poly-D-lysine (PDL), respectively. ε-Polylysine (ε-poly-L-lysine, EPL) is typically produced as a homopolypeptide of approximately 25-30 L-lysine residues. ε-Poly-L-lysine is commonly used as a preservative in food products. In further embodiments, the peptides, peptide analogs, and peptidomimetics may be polyornithine such as poly-1-ornithine. Such polylysines or polyornithine may be incorporated into larger peptides, which may or may not include additional furin binding site sequences, and in some embodiments, the polylysines may be modified by any of the means discussed above.

In some embodiments, the protease inhibitor may be a small molecule protease inhibitors such as, candoxatril, candoxatrilat, dexecadotril (retorphan), ecadotril (sinorphan), racecadotril (acetorphan), sacubitril, sacubitril, thiorphan, UK-414,495, aladotril, alatriopril, daglutril, fasidotril, gemopatrilat, ilepatril, ketalorphan, omapatrilat, phosphoramidon, RB-101, sampatrilat, spinorphan, dynorphin, trypsin, aloxistatin, camostat, ecallantide, leupeptin, nafamostat, pacifastins, patamostat, pepstatin, sepimostat, sivelestat, talopeptin, ulinastatin, upamostat, aliskiren, cipro keren, detikinet, enalkiren, pepstatin, remikiren, terlakiren, zankiren, and the like and combinations thereof. Such small molecule protease inhibitors may inhibit endoprotease activity of metalloproteases such as, neprilysin and thermolysin, cysteine proteases, serine proteases, threonine proteases, tryptase, chymotrypsin, kallikreins, renin, aspartyl proteases, neutrophil elastases, and the like and combinations thereof. In certain embodiments, the small molecule protease inhibitor may be a serine protease inhibitor such as alpha-1 proteinase inhibitor, antithrombin III, avidin, bivalirudin, desirudin, lepirudin, leupeptin, sepimostat, upamostat, and the like, and in some embodiments, the small molecule protease inhibitor may selectively inhibit furin endoprotease.

The protease inhibitor can be provided in any therapeutically effective amount. For example, the compositions of embodiments may include up to about 95% (w/w), about 5% (w/w) to about 90% (w/w), about 10% (w/w) to about 75% (w/w), about 20% (w/w) to about 50% (w/w), or any range or individual concentration of protease inhibitor encompassed by these example ranges.

In some embodiments, the compositions may contain one or more additional active agents that is provided in addition to the protease inhibitor, and in certain embodiments, the additional active agent may be antiviral agents. Antiviral agents include, for example, abacavir sulfate, acyclovir, amantadine hydrochloride, amprenavir, cytarabine, delavirdine mesylate, didanosine, edoxudine, efavirenz, famciclovir, floxuridine, fomivirsen, foscarnet, ganciclovir, idoxuridine, indinavir, lamivudine, lamivudine/zidovudine, nelfinavir mesylate, nevirapine, oseltamivir phosphate, penciclovir, ribavirin, rimantadine hydrochloride, ritonavir, saquinavir, saquinavir mesylate,stavudine, sorivudine, trifluridine, valaciclovir, vidarabine, kethoxal, methisazone, moroxydine, podophyllotoxin, ribavirin, rimantadine, stallimycine, statolon, tromantadine, xenozoic acid, zalcitabine, zanamivir, zidovudine, and the like and combinations thereof. Such active agents can be provided in any therapeutically effective amount. For example, the compositions of embodiments may include up to about 15% (w/w), about 0.25% (w/w) to about 15% (w/w), about 0.5% (w/w) to about 10% (w/w), about 0.75% (w/w) to about 7.5% (w/w), about 1% (w/w) to about 5% (w/w), about 1% (w/w) to about 3% (w/w), or any range or individual concentration of active agent encompassed by these example ranges.

In some embodiments, the compositions may further include an anti-inflammatory compound such as hyaluronic acid, curcumin, glutathione, methotrexate, tofacitinib, 6-mercaptopurine, azathioprine sulfasalazine, mesalazine, olsalazine chloroquine/hydroxychloroquine, penicillamine, aurothiomalate (intramuscular and oral), azathioprine, colchicine, corticosteroids (oral, inhaled, and local injection), a beta-2 adrenoreceptor agonist (salbutamol, terbutaline, salmeterol), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e. g. prednisolone), a phosphodiesterase inhibitor, an adenosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-1 0, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCV acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCI0-469, VX-702, AMG-548, VX-740, Roflumilast, IC-485, CDC-801, S1PI agonists (such as FTY720), a PKC family inhibitor (e.g. Ruboxistaurin or AEB-071) or Mesopram, budesonide; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), an anti-inflammatory cytokine (e.g. IL-4, IL-1 0, IL-11, IL-13 or TGF), therapeutic agents that target an intrinsic checkpoint blockade, such as, for example, the gene encoding Cytokine-inducible $SH_2$-containing protein (CISH), antibody BGB-A317, Nivolumab, or Pembrolizumab, atezolizumab, avelumab, durvalumab, ipilimumab, and the like and combinations thereof. The amount of anti-inflammatory agent is not limited and includes any therapeutically effective amount. For example, in some embodiments, the amount of anti-inflammatory agent may be about 0.01 wt. % to about 5 wt %, relative to the total amount of the composition, about 0.1 wt. % to about 1 wt %, relative to the total amount of the formulation, or any range or individual concentration encompassed by these example ranges.

In some embodiments, the compositions may further include pharmaceutical and/or cosmetically acceptable carries, excipients, diluents, fillers, disintegrants, desiccants, binders, lubricants, surfactants, hydrophobic vehicles, water soluble vehicles, emulsifiers, buffers, humectants, moisturizers, solubilizers, preservatives, colorants, plasticizers, carriers, or combinations thereof. The person of ordinary skill in the art can refer to various pharmacologic references such as, for example, Modern Pharmaceutics, Banker & Rhodes, Marcel Dekker, Inc. (1979) and Goodman & Gilman's The Pharmaceutical Basis of Therapeutics, 6th Edition, MacMillan Publishing Co, New York (1980) for guidance in determining the amount of such components in the compositions and formulations of embodiments. Any previously mentioned, carries, excipients, diluents, fillers, disintegrants, desiccants, binders, lubricants, surfactants, hydrophobic vehicles, water soluble vehicles, emulsifiers, buffers, humectants, moisturizers, solubilizers, preservatives, colorants, plasticizers, carriers, and combinations thereof may be incorporated into such compositions.

In some embodiments, the composition may include a solvent such as water, isopropyl alcohol, dipropylene glycol methyl-ether, butylated hydroxytoluene dipropylene glycol monomethyl-ether, 1-methoxy 2-propanol (glysolv PM/Icinol PM), Ethylene glycol monobutylether (butyl glysolv/butylicinol), Butyl diglysolv1(butyl-icinol), transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as Aloe vera derivatives or sesame seed oil or derivatives thereof, ethosomes, azone, castor oil derivatives, such as ethoxylated castor oil, jojoba oil derivatives, corn oil derivatives, emu oil derivatives, and the like and combinations thereof. The solvent can be present in any concentration. For example, in some embodiments, the solvent may be of about 5% (w/w) to about 99.9% (w/w), about 10% (w/w) to about 95% (w/w), about 25% (w/w) to about 90% (w/w), about 20% (w/w) to about 80% (w/w), or any range or individual concentration of solvent encompassed by these example ranges.

In some embodiments, the composition may include a polar water-miscible solvent, such as an alcohol or glycol. Polar water-miscible solvents may improve skin penetration and solvation of the active agent. The polar water-miscible solvent may be, for example, $C_1$-$C_4$ alcohols, polyethylene glycol, ethylene glycol, propylene glycol, butylene glycol, pentylene glycol, glycerol, diethylene glycol monoethyl ether, propylene carbonate, and the like and combinations and mixtures thereof. The total amount of polar water-miscible solvent may be less than about 10 wt % by weight of the total composition, about 0.5% (w/w) to about 10% (w/w), about 1% (w/w) to about 5% (w/w), about 0.5% (w/w) to about 5% (w/w), or any range or individual concentration of solvent encompassed by these example ranges.

In some embodiments, the compositions may include a surfactant. The surfactant may be incorporated into the oil phases, the aqueous phase, or both. Suitable surfactants include, for example, alkyl polyglycol ethers, alkyl polyglycol esters, ethoxylated alcohols, polyoxyethylene sorbitan fatty acid esters, polyoxyethylene fatty acid esters, ionic or non-ionic surfactants, hydrogenated castor oil/polyoxyethylene glycol adducts, castor oil/polyoxyethylene glycol adducts, sorbitan fatty acid esters (such as Span 20 or Span 80), block copolymers of ethylene oxides and propylene oxides (such as Pluronic L121 or Pluronic F68), polymeric surfactants having crosslinked copolymers of acrylic acid, such as Pemulen Tr-1 and Pemulen Tr-2, and the like and combinations and mixtures thereof. The composition may include surfactant in a concentration of about 0.1 wt % to about 5 wt %, about 0.5 wt % to about 3 wt %, about 0.7 to about 2 wt %, or any range or individual concentration of solvent encompassed by these example ranges.

In some embodiments, the compositions may include an antioxidant. Such antioxidant may be, for example, butylated hydroxytoluene, ascorbic acid, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherol, and the like and pharmaceutically acceptable salt or ester thereof or combinations thereof. The antioxidant can be present in a concentration of about 0.01% (w/w) to about 1% (w/w) of the total composition or any individual concentration encompassed by this example range.

In some embodiments, the composition may include an emulsifying agent including, for example, various monoglycerides, diglycerides, triglycerides, and blends thereof at a concentration of about 3% (w/w) to about 10% (w/w) of the total composition.

In some embodiments, the composition may further include an analgesic agent such as, for example, methyl salicylate, codeine, morphine, methadone, pethidine, buprenorphine, hydromorphone, levorphanol, oxycodone, fentanyl, a non-steroidal anti-inflammatory drug (NSAID), and the like and combinations thereof. The amount of the analgesic agent in such compositions may be about 0.01% (w/w) to 5% (w/w) of the total composition.

In some embodiments, the composition may further include a moisturizing agent. Examples of moisturizing agents useful in the compositions of this invention include propylene glycol, glycerin and the like and combinations thereof. The amount of moisturizing agent in such compositions may be about 0.01% (w/w) to 10% (w/w) of the total composition.

In some embodiments, the composition may further include a pharmaceutically acceptable buffer sufficient to adjust and maintain the pH of the compositions of the present invention in the range of about 7.0 to about 14.0, preferably about 8.5 to about 12.0. Typically suitable buffers include citrate, phosphate, glycine, and the like. The amount of buffer in such compositions may be about 0.01% (w/w) to 10% (w/w) of the total composition In some embodiments of the present invention, compositions may further contain a mineral, mineral salt, or combinations thereof. Such minerals are not limited, and can include selenium, sulfur, zinc, iron, chlorine, cobalt, copper, manganese, molybdenum, and iodine. The amount of the mineral or mineral salts in the topical formulation is not limited, and includes any therapeutically effective amount. For example, the mineral or mineral salt may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments of the present invention, the compositions may further include a vitamin or a combination of vitamins. Vitamins are organic molecules that are essential nutrients that organisms need to sustain proper biological function and metabolism. The vitamins encompassed by the invention are not limited, and can be, for example, vitamin A, vitamin $B_1$, vitamin $B_2$, vitamin $B_3$, vitamin $B_4$, vitamin $B_5$, vitamin $B_6$, vitamin $B_7$, vitamin $B_8$, vitamin $B_9$, vitamin $B_{10}$, vitamin $B_{11}$, vitamin $B_{12}$, vitamin C, vitamin D, vitamin E, and vitamin K. The amount of the vitamin in the topical formulation is not limited, and can be any therapeutically effective amount. For example, the vitamin may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

The compositions may be formulated for delivery to affected tissue. For example, in some embodiments, the composition may be in the form of a nasal spray. Nasal sprays are used to deliver medications locally in the nasal cavities or systemically. Variations of nasal sprays include nasal drops, nasal ointments, nasal injections, nasal washes, nasal packings. The nasal sprays of embodiments may include a solvent and preservative in addition to the protease inhibitor to produce a liquid or gel composition. In some embodiments, such nasal sprays may further include a moisturizer or wetting agent to improve patient comfort during administration.

In other embodiments, the composition may be in the form of eye drops. Eye drops are saline-containing drops used as an ocular route to administer. Depending on the condition being treated, they may contain steroids, antihistamines, sympathomimetics, beta receptor blockers, parasympathomimetics, parasympatholytics, prostaglandins, nonsteroidal anti-inflammatory drugs (NSAIDs), antibiotics, antifungals, or topical anesthetics.

The compositions of embodiments described above may be administered to the nose, mouth, eyes, or ears of a subject. In various embodiments, the step of administering can be carried out before, during, or after exposure to an infectious agent, such as a virus or bacteria. In particular embodiments, the compositions described above may have a general antiviral effect. Viruses treated using the compositions and methods of embodiments are not limited. For example, the viral infections may be caused by varicella zoster virus (VSV/HHV-3), Epstein-Barr virus (EBV/HHV-4), cytomegalovirus (CMV/HHV-5), coronavirus (COVID-19), human papillomavirus, infectious mononucleosis, human Influenza A (H3N2), human Influenza B (H1N1), molluscum contagiosum, rhinoviruses, and enteroviruses and the like and combinations thereof.

In certain embodiments, the compositions of the invention may be used prophylactically to hinder or eliminate host protease mediated cleavage of viral particles necessary to infect host cells. For example, prophylactically administered polylysine containing compositions have been shown to eliminate COVID-19 infections in individuals repeatedly exposed to the COVID-19 virus for both healthy and high risk subjects.

Further embodiments are directed to methods for treating infections either prophylactically or after the onset of symptoms. Such methods may include the steps of administering an effective amount of any of the compositions described above to the nose, eyes, ears, or mouth of a subject in need of treatment. In some embodiments, the step of administering can be carried out one or two times per hour, one, two, or three times per day, one, two, three, four, or more times per week, and so on depending on the period of exposure or severity of symptoms.

The step of administering can be carried out by various means. For example, administering can be accomplished by injecting the composition to the nasal cavity of a subject in need of treatment. In some embodiments, administering may include injecting the composition to the eyes of a subject in need of treatment. In further embodiments, administration can be accomplished by injecting the composition into the ear canal of a subject in need of treatment. in yet other embodiments, administering can be accomplished by orally ingesting the composition. As is known in the art, certain means for administering may require the use of particular components of the formulation. Such components are described above and can be appropriately incorporated into the compositions.

In some embodiments, the methods may include the steps of administering any of the compositions of the invention described above and co-administering one or more of the additional active agents described above, antivirals described above, anti-inflammatory agents described above, and the like. Such additional active agents, antivirals, and anti-inflammatory agents can be administered in separate dosages by any administration route. For example, a composition of the invention can be administered topically by, for example, intranasal spray, and the additional active agents, antivirals, anti-inflammatory agents, and combinations thereof may be administered separately topically, orally, or by injection.

The methods of various embodiments may be used prophylactically to reduce the likelihood of infection. The protease inhibitors may bind to and inhibit proteases required for viral infection reducing the likelihood of infection when the subject to whom the compositions of the invention have been administered is challenged by exposure to the virus. In addition, the protease inhibitors may further reduce the titer of viral particles contacting a subject to whom the compositions of the invention have been administered. For example, in some embodiments, administering the compositions of the invention may reduce viral titers by at least 80%, at least about 70%, at least about 60%, at least about 50%, about 20% to about 80%, about 20% to about 70%, about 20% to about 60%, about 20% to about 50%, or any range or individual value encompassed by these example ranges. Such prophylactic administration may reduce the likelihood of infection by at least about 99%, at least about 95%, at least about 90%, at least about 80%, at least about 75%, at least about 50% or any range or individual value encompassed by these example ranges.

The methods of some embodiments can be used to treat infected subjects who may or may not be exhibiting symptoms of the disease. In such embodiments, the compositions may reduce viral load in given volume of bodily fluid such as, sputum or blood plasma by at least about 80%, at least about 70%, at least about 60%, at least about 50%, about 20% to about about 80%, about 20% to about 70%, about 20% to about 60%, about 20% to about 50%, or any range or individual value encompassed by these example ranges. In some embodiments, the methods may improve the time to recovery by at least about 10%, at least 20%, at least about 30%, at least about 40%, at least about 50%, about 5% to about about 50%, about 10% to about 40%, about 10% to about 30%, about 5% to about 20%, or any range or individual value encompassed by these example ranges, reducing the time to recovery from about 10 days to 14 days to about 2 to about 7 days. The survival rate of viral infection may increase by at least about 30%, at least about 40%, at least 50%, at least 75%, or any range or individual value encompassed by these example ranges. In addition, reduced viral load may reduce the long term effects of infection such as damage to the subject's lungs, heart, and brain and symptoms including fatigue, shortness of breath, cough, joint pain, chest pain, muscle pain or headache, fast or pounding heartbeat, loss of smell or taste, faltering memory, loss of concentration, sleep problems and insomnia, rash, hair loss, and the like and various combinations thereof.

Reduction of viral titer and viral load in subjects infected with or exposed to the virus may further reduce the rate mutation to viral DNA, reducing the mutation rate of the virus, suppressing the outbreak of viral variants, and limiting the spread of such variants. As such fewer and less frequent vaccines will be necessary to contain and reduce outbreaks of variants.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

A high risk male was administered a composition containing polylysine twice daily as a prophylactic treatment for COVID-19. The subject was directly exposed to a confirmed COVID-19 positive individual for 40 minutes. The subject was exposed to virus positive individuals at a public hospital intake, processing, pre-op, and recovery after 4 separate procedures under anesthesia and had intubation. The subject never developed symptoms and tested negative for COVID-19 twice after two days in public hospital.

It was an intra-nasal spray via a metered dose intranasal spray. It was formulated in sterile saline at a usage level of 0.003% and was applied twice daily for 5 days after the initial insult. Because a repeat confirmed Coronavirus exposure happened on day 2, the treatment was extended for a total of 4 days post exposure. The car had 3 people in it including the subject, the symptomatic subject who tested positive the following morning and a 3rd who was asymptomatic but developed symptoms 4 days later and then tested positive. The patient was tested twice with the second one 10 days after first exposure. He was negative both times and never developed symptoms.

Example 2

Seven individuals were subjected to multiple very high risk exposures with confirmed COVID-19 patients. None of the individuals developed symptoms after exposure and returned negative COVID-19 test results 2 weeks out. Untreated individuals exposed confirmed COVID-19 under the same condition developed symptoms.

Example 3

Figure 1:
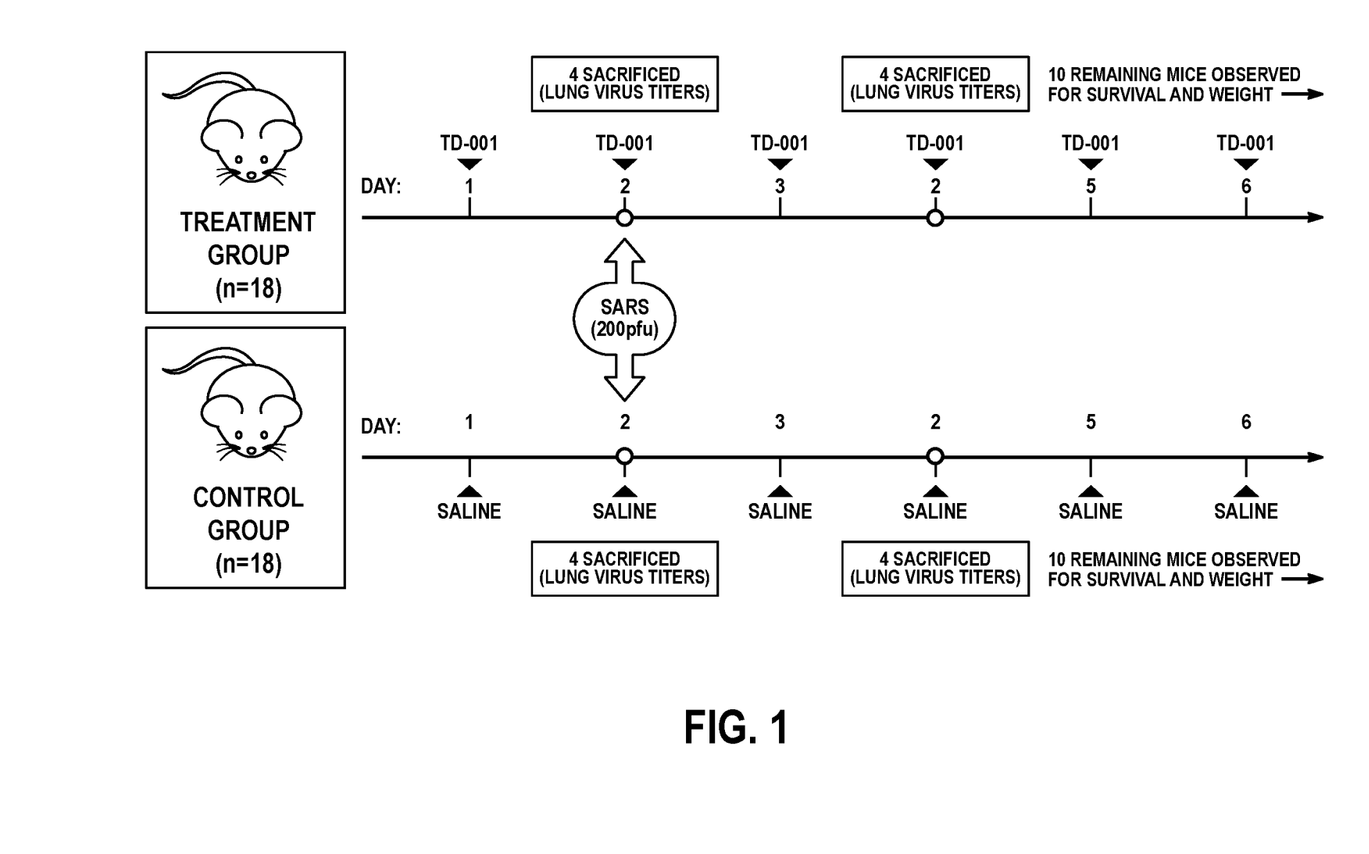

Thirty-six mice were treated daily with nebulized polylysine or saline before and after exposure to high titer SARS-COV2. As illustrated in FIG. 1, half of the mice (n=18) were administered nebulized polylysine daily and the other half (n=18) were administered nebulized polylysine daily for 6 days. Both cohorts were exposed to 200 pfu of SARS-CoV-2 on Day 2. 200 pfu is typically lethal dose for mice and is the equivalent of 600,000 pfu in humans, adjusted for weight. Humans develop the disease after contact with as few as 10 pfu SARS. Four mice from each cohort were sacrificed on day 2, and four mice from each cohort were sacrificed on day 4 to measure viral load via lung titers.

Figure 2:
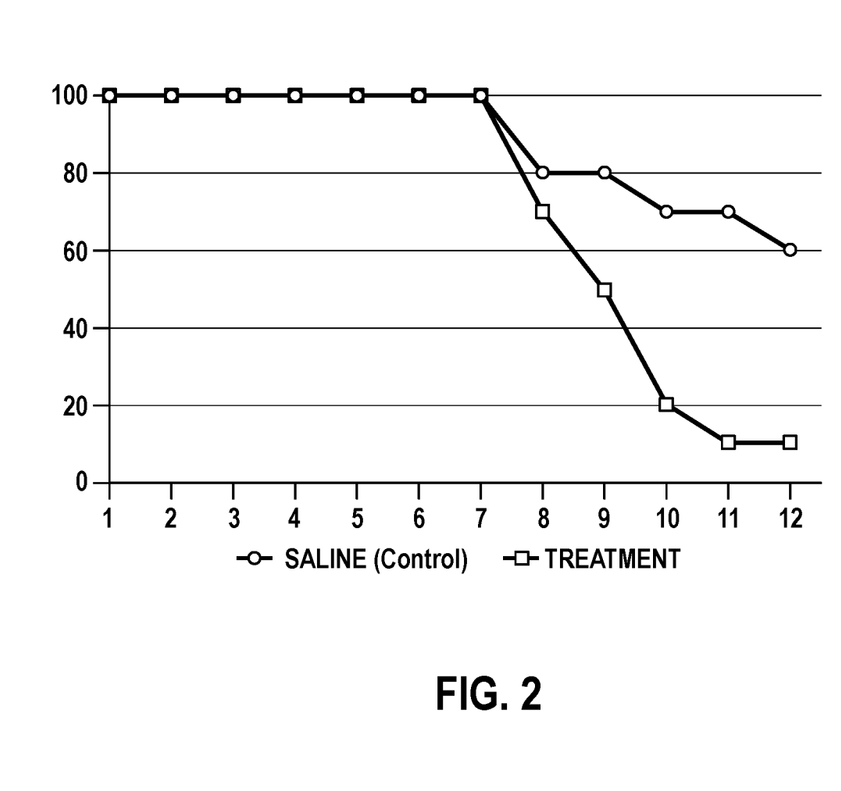

Mice that were nebulized polylysine exhibited a 5 fold increase in total survival across the treatment period. Overall, six of ten of the polylysine group survived the treatment and exposure period, while only 1 mouse associated with the control group survived, resulting in a highly significant improvement in time to event ($p<0.001$). See FIG. 2.

Figure 3A:
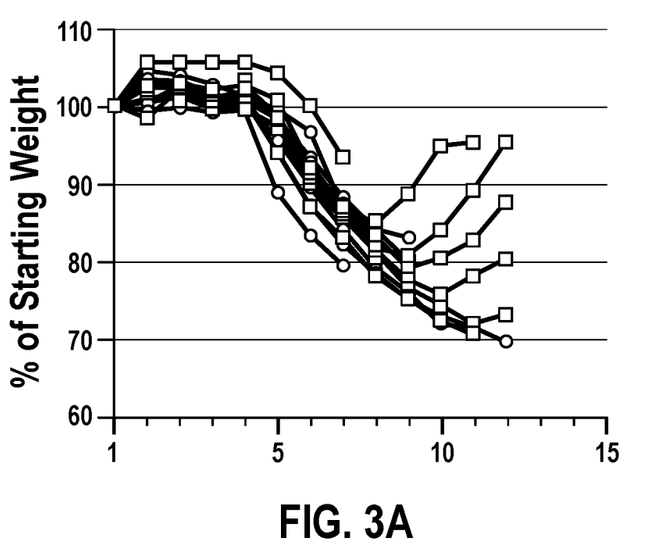
Figure 3B:
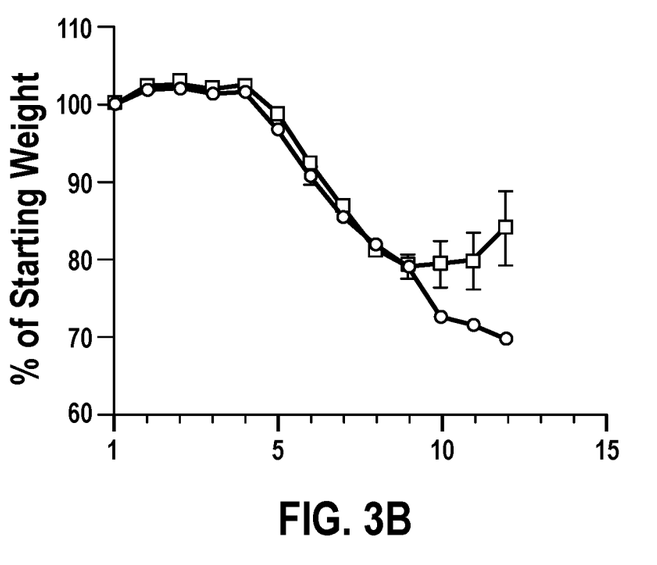

Following the treatment and exposure period, mice administered polylysine began to recover as indicated by an increasing weight to near pre-treatment levels ($p<0.05$). See FIG. 3A (individual weight) and FIG. 3B (average weight per cohort). In contrast, the surviving mouse from the control group continued to lose weight 7 days after the treatment and exposure period ended, suggesting that this mouse was unable to recover from the viral challenge.

These data show that intranasal administration of polylysine improves the both survival and recovery of subjects challenged by SARS virus, including COVID-19, exposure. Dosing optimization offers potential to further enhance this effect.

Example 4

Thirty mice were treated daily with nebulized polylysine or saline before and after exposure to high titer SARS-COV2. Half of the mice (n=15) were administered nebulized polylysine daily and the other half (n=15) were administered nebulized polylysine daily for 6 days. Both cohorts were exposed to 10,000 pfu of SARS-CoV-2 on Day 2. Four mice from each cohort were sacrificed on day 2, and four mice from each cohort were sacrificed on day 4 to measure viral load via lung titers.

Figure 4:
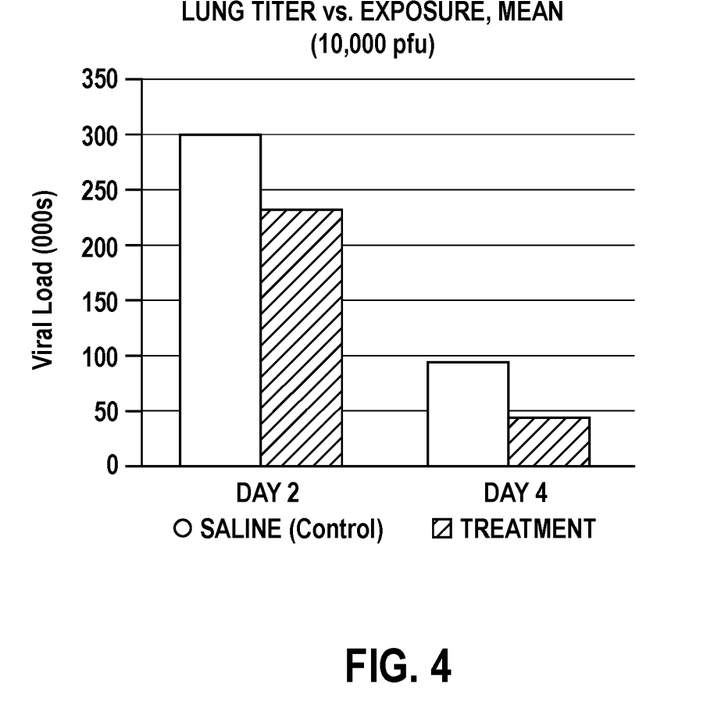
Figure 5:
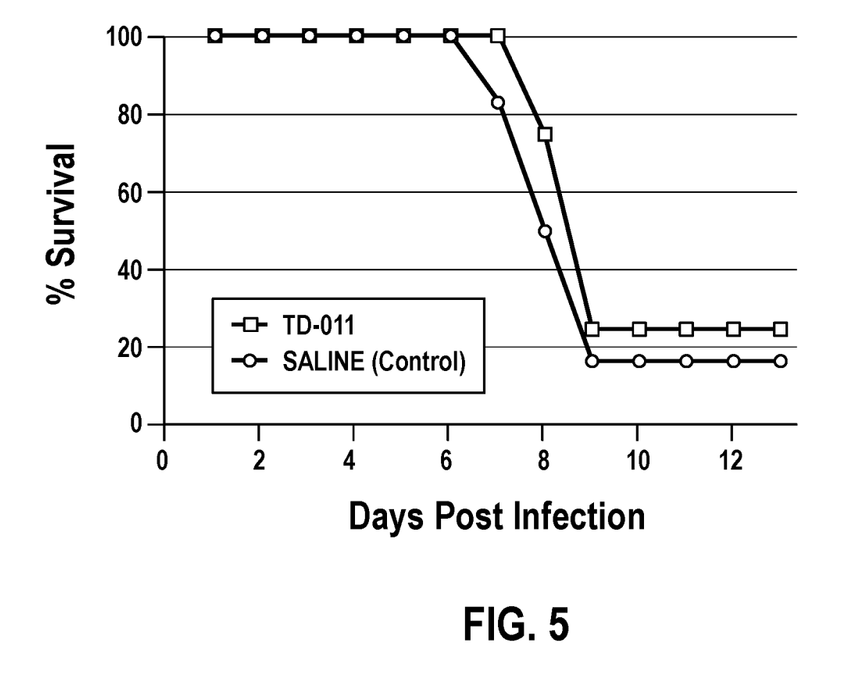

Despite acute exposure to 10,000 active viral particles per animal, notable viral titer reductions in the lungs of exposed mice were observed. A large reduction in initial infections after exposure (23% reduction after initial exposure on Day 2) was observed for mice that were administered polylysine. This reduction in viral load expanded by Day 4, producing a 54% reduction in viral load compared to control mice. See FIG. 4. This represents an improved survival rate of 50% and delayed onset of morbidity with a highly statistically significant time to event (P<0.001). See FIG. 5.

```
SEQUENCE LISTING

Sequence total quantity: 4
SEQ ID NO: 1           moltype = AA   length = 4
FEATURE                Location/Qualifiers
source                 1..4
                       mol_type = protein
                       organism = synthetic construct
SEQUENCE: 1
RRGR                                                                            4

SEQ ID NO: 2           moltype = AA   length = 6
FEATURE                Location/Qualifiers
source                 1..6
                       mol_type = protein
                       organism = synthetic construct
SEQUENCE: 2
RKRKKR                                                                          6

SEQ ID NO: 3           moltype = AA   length = 6
FEATURE                Location/Qualifiers
source                 1..6
                       mol_type = protein
                       organism = synthetic construct
SEQUENCE: 3
RRRKKR                                                                          6

SEQ ID NO: 4           moltype = AA   length = 6
FEATURE                Location/Qualifiers
source                 1..6
                       mol_type = protein
                       organism = synthetic construct
SEQUENCE: 4
RKRKKR                                                                          6
```

The invention claimed is:

1. A method for treating a subject infected by a severe acute respiratory virus, comprising: administering to a subject in need of treatment a composition comprising a furin binding compound, wherein the furin binding compound is selected from the group consisting of polylysine, α-polylysine, and ε-polylysine, and a pharmaceutically acceptable carrier.

2. The method of claim 1, wherein administering comprises topical administration to an eye, ear, or nose of the subject.

3. The method of claim 1, wherein administering comprises administering an intranasal spray.

4. The method of claim 1, wherein administering comprises administering at least once per day.

5. The method of claim 1, whereby said administering reduces viral load in patient sputum or blood plasma by at least about 20%.

6. The method of claim 1, whereby said administering improves time to recovery by at least about 20%.

7. The method of claim 1, wherein the severe acute respiratory virus is SARS-CoV-2.

8. The method of claim 7, wherein the subject is suffering from COVID-19.

9. The method of claim 8, whereby said administering reduces long term effects of COVID-19.

10. The method of claim 1, wherein the furin binding compound comprises about 95% (w/w) to about 5% (w/w) furin binding compound based on the total weight of the composition.

11. The method of claim 1, wherein the composition further comprises an antiviral agent.

12. The method of claim 1, further comprising administering an antiviral agent or an anti-inflammatory agent with the composition.

13. The method of claim 12, wherein administering the antiviral agent or anti-inflammatory agent comprises administration simultaneously or sequentially with the composition.

14. The method of claim 12, wherein administering the antiviral agent or anti-inflammatory agent comprises administration via oral administration or by injection.

15. The method of claim 11, wherein the antiviral agent is acyclovir, amantadine hydrochloride, amprenavir, cytarabine, delavirdine mesylate, edoxudine, efavirenz, famciclovir, floxuridine, fomivirsen, foscarnet, ganciclovir, idoxuridine, indinavir, lamivudine, nelfinavir mesylate, nevirapine, oseltamivir phosphate, penciclovir, ribavirin, rimantadine hydrochloride, ritonavir, saquinavir, saquinavir mesylate, sorivudine, trifluridine, valaciclovir, vidarabine, kethoxal, methisazone, moroxydine, podophyllotoxin, ribavirin, rimantadine, stallimycine, statolon, tromantadine, xenozoic acid, zalcitabine, zanamivir, or combinations thereof.

16. The method of claim 1, wherein the composition further comprises an anti-inflammatory agent.

17. The method of claim 16, wherein the anti-inflammatory agent is hyaluronic acid, curcumin, glutathione, methotrexate, tofacitinib, 6-mercaptopurine, azathioprine sulfasalazine, mesalazine, olsalazine chloroquine/hydroxychloroquine, penicillamine, aurothiomalate, azathioprine, colchicine, corticosteroids, a beta-2 adrenoreceptor agonist, a xanthine, cromoglycate, nedocromil, ketotifen, ipratropium and oxitropium, cyclosporin, FK506, rapamycin, mycophenolate mofetil, leflunomide, a corticosteroid, a phosphodiesterase inhibitor, an adenosine agonist, an antithrombotic agent, a complement inhibitor, an adrenergic agent, TNF, IL-1, an IL-1 converting enzyme inhibitor, a T-cell signaling inhibitor, a metalloproteinase inhibitor, sulfasalazine, a 6-mercaptopurine, an angiotensin converting enzyme inhibitor, a soluble cytokine receptor, an anti-inflammatory celecoxib, folic acid, cytokine, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCL, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCV acetaminophen, olopatadine HCl misoprostol, omeprazole, cyclophosphamide, rituximab, IL-1 TRAP, MRA, CTLA4-IG, IL-18 BP, anti-IL-12, Anti-ILIS, BIRB-796, SCI0-469, VX-702, AMG-548, VX-740, Roflumilast, IC-485, CDC-801, SIPI agonists, a PKC family inhibitor, Mesopram, budesonide; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors; a cell surface molecule; methotrexate; cyclosporine; FK506; rapamycin; mycophenolate mofetil; leflunomide; a corticosteroid; a phosphodiesterase inhibitor; an adenosine agonist; an antithrombotic agent; a complement inhibitor; an adrenergic agent; an agent that interferes with signaling by proinflammatory cytokines, TNF 5, or IL-1; an IL-1 converting enzyme inhibitor; a TNF converting enzyme inhibitor; a T-cell signaling inhibitor, or a kinase inhibitor; a metalloproteinase inhibitor; sulfasalazine; azathioprine; a 6-mercaptopurine; an angiotensin converting enzyme inhibitor; a soluble cytokine receptor, an anti-inflammatory cytokine, the gene encoding Cytokine-inducible $SH_2$-containing protein (CISH), antibody BGB-A317, Nivolumab, or Pembrolizumab, atezolizumab, avelumab, durvalumab, ipilimumab; and combinations thereof.

18. A method for treating a subject infected by a severe acute respiratory virus, comprising: administering to a subject in need of treatment a composition comprising a furin binding compound, wherein the furin binding compound is selected from the group consisting of a peptide, a peptide analog, and a peptidomimetic.

19. The method of claim 18, wherein the furin binding compound has a polyarginine sequence.

20. The method of claim 19, wherein the polyarginine sequence is RKRKKR (SEQ ID NO:2), RKKR (SEQ ID NO:3), or RRRKKR (SEQ ID NO:4).

\* \* \* \* \*